United States Patent [19]

Wang et al.

[11] Patent Number: 5,382,713

[45] Date of Patent: Jan. 17, 1995

[54] PHENOLIC COMPOUNDS

[75] Inventors: Pen C. Wang, Houston; Donald R. Kelsey, Fulshear, both of Tex.

[73] Assignee: Shell Oil Company, Houston, Tex.

[21] Appl. No.: 13,837

[22] Filed: Feb. 5, 1993

[51] Int. Cl.⁶ .............................................. C07C 39/17
[52] U.S. Cl. .................................... 568/734; 525/523; 525/534; 528/103; 568/718; 568/719; 568/721; 568/732; 568/733
[58] Field of Search ............... 568/732, 718, 719, 721, 568/733, 734; 525/534, 523; 528/103

[56] References Cited

U.S. PATENT DOCUMENTS

| | | | |
|---|---|---|---|
| 3,536,734 | 10/1970 | Vegter et al. | 260/348.6 |
| 4,067,899 | 1/1978 | Mardiguin | 568/734 |
| 4,112,000 | 9/1978 | Mardiguin | 568/734 |
| 4,239,920 | 12/1980 | Del Conte | 568/734 |
| 4,301,306 | 11/1981 | Layer | 568/719 |
| 4,301,311 | 11/1981 | Müller et al. | 568/734 |
| 4,484,010 | 11/1984 | Layer | 568/732 |
| 4,764,571 | 8/1988 | Namba et al. | 525/534 |
| 5,095,082 | 3/1992 | Kelsey | 526/282 |

FOREIGN PATENT DOCUMENTS 466263 1/1992 European Pat. Off. ............ 568/721

Primary Examiner—Werren B. Lone

[57] ABSTRACT

A phenolic compound is provided which can be described by the formula

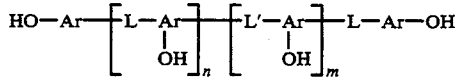

in which Ar is a $C_{6-20}$ aromatic moiety, L is a cyclohexanenorbornane linking moiety, L' is a divalent cycloaliphatic moiety, and each of m and n is a number within the range of 0 to about 10. Such phenols include the product of the addition reaction of phenol with a cyclohexenenorbornene compound such as 5-(3-cyclohexen-1-yl)bicyclo[2.2.1]hept-2-ene.

10 Claims, No Drawings

PHENOLIC COMPOUNDS

BACKGROUND OF THE INVENTION

This invention relates to novel phenolic compounds. In one embodiment, the invention relates to phenolic curing agents for epoxy resins.

Polyphenolic compounds are useful as curing agents for epoxy resins. When used as a component of an epoxy resin-based electrical lamination formulation, it is desirable for both the epoxy resin and the curing agent to have a low melt viscosity, as formulations which can be applied to glass fibers in the melt, rather than in solution, are favored.

It is therefore an object of the invention to provide novel phenolic compounds. It is an object of one aspect of the invention to provide polyphenols which have a low melt viscosity.

SUMMARY OF THE INVENTION

According to the invention, a phenolic compound is provided which can be described by the formula

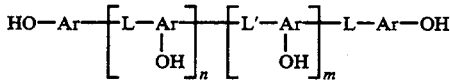

in which Ar is a $C_{6-20}$ aromatic moiety, L is a cyclohexanenorbornane linking moiety, L' is a divalent cycloaliphatic moiety, and each of m and n is a number within the range of 0 to about 10. Such polyphenols include the product of the addition reaction of one or more phenols with a cyclohexenenorbornene such as 5-(3-cyclohexen-1-yl)bicyclo[2.2.1]hept-2-ene, and optionally dicyclopentadiene, in the presence of an addition catalyst such as boron trifluoride etherate. The resulting polyphenols are useful as curing agents for epoxy resins and as precursors of thermosetting resins such as epoxy resins and cyanate ester resins.

DETAILED DESCRIPTION OF THE INVENTION

The invention polyphenols can be prepared by the addition reaction of a phenol with a cyclohexenenorbornene compound such as 5-(3-cyclohexen-1-yl)bicyclo[2.2.1]hept-2-ene. Suitable phenols include mono and polynuclear phenol s having at least one unsubstituted position ortho- or para- to a phenolic hydroxyl group, such as phenol, cresol, 3,4- and 3,5-dimethylphenol, resorcinol, biphenol, 1-naphthol and bisphenol A or F. Phenol is preferred.

Suitable cyclohexenenorbornene compounds include

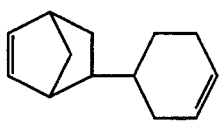

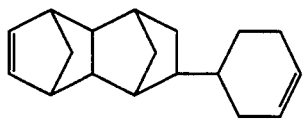

-continued

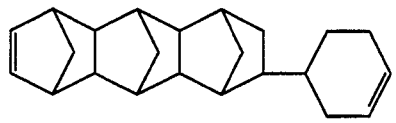

referred to herein as "monoadduct," "diadduct" and "triadduct," respectively, and isomers thereof.

The cyclohexenenorbornene is an adduct of 4-vinylcyclohexene and cyclopentadiene which can be prepared by contacting 4-vinylcyclohexene and dicyclopentadiene, preferably in the presence of a polymerization inhibitor such as t-butyl catechol, at a temperature of at least about 180° C., preferably about 220° to 260° C., for a time within the range of about 2 hours to about 8 hours. Under these conditions, the dicyclopentadiene is cracked to cyclopentadiene, and the vinylcyclohexene and cyclopentadiene undergo an addition reaction to produce a mixture of mono-, di- and poly-adducts along with cyclopentadiene oligomers (e.g., trimer, tetramer, pentamer, etc.). The reaction product mixture containing predominately 5-(3-cyclohexen-1-yl)-2-norbornene (monoadduct) is allowed to cool to about 50°-70° C. and is stirred under reduced pressure to strip off unreacted vinylcyclohexene. The reaction product is then purified by fractional vacuum distillation to remove by-products including, optionally, di- and poly-adducts and cyclopentadiene oligomers, and the purified product is passed through an adsorbent bed for removal of t-butyl catechol. Preparation of a vinylcyclohexene/cyclopentadiene adduct is illustrated in Example 1 herein.

The invention polyphenols can optionally include a residue L' of a cyclic diene such as, for example, dicyclopentadiene, cyclopentadiene, norbornadiene dimer, norbornadiene, methylcyclopentadiene dimer, limonene, 1,3- and 1,5-cyclooctadiene. α- and γ-terpinene, 5-vinylnorbornene, 5-(3-propenyl)-2-norbornene, and cyclopentadiene oligomers. The preparation of such a phenol is illustrated in Example 4 herein.

The phenol/adduct reaction is generally carried out by contacting, under addition reaction conditions, the vinylcyclohexene/cyclopentadiene adduct and optional cyclic diene with a molar excess, preferably about 10 to about 30 moles, of the selected phenol per mole of the adduct. The reaction is most efficiently carried out in the presence of a Lewis acid addition catalyst such as $BF_3$, coordination complexes thereof such as boron trifluoride etherate, $AlCl_3$, $FeCl_3$, $SnCl_4$, $ZnCl_2$, silica and silica-alumina complexes and at an elevated temperature within the range of about 70° to about 200° C., preferably about 100° to about 180° C. The reaction is continued until the desired degree of reaction has been completed, usually for a time within the range of about 30 minutes to about 10 hours, generally about 1 hour to about 3 hours. Preparation of such polyphenols is illustrated in Examples 2, 4, 5 and 6 herein.

The invention phenolic compound can be combined with an epoxy resin by, for example, melt-blending, preferably in the presence of a curing catalyst such as an imidazole. Subsequent cure of the epoxy resin is effected by heating the epoxy/phenol mixture at a temperature above about 150° C., preferably within the range of about 200° to about 300° C., for at least about 0.25 hour. Cure of epoxy resins with invention phenols is illustrated in Examples 7, 8 and 9 herein.

The invention polyphenols are useful as curing agents for epoxy resins, as precursors for thermasettable resins such as epoxy resins and cyanate ester resins, and as stabilizing additives for thermoplastics. The invention epoxy resin compositions are useful in molding powder, coating and electrical encapsulation and laminating applications.

EXAMPLE 1

Preparation of 5-(3-cyclohexen-1-yl)bicyclo[2.2.1]hept-2-ene

Dicyclopentadiene and 4-vinylcyclohexene in equimolar mixture were heated in an autoclave at 240° C. for 4–4.5 hours. The reaction product was diluted with cyclohexane and passed through a packed bed of alumina to remove the t-butylcatechol inhibitor introduced with the reactants. The resulting product mixture was distilled in a wiped film evaporator at 3 mm Hg pressure at 90° C. to produce a light fraction containing unreacted vinylcyclohexene and dicyclopentadiene and the mono-adducts of 4-vinylcyclohexene and cyclopentadiene. A 150 g sample of this distillate was vacuum distilled using a 10-tray Oldershaw column to give four fractions. The fourth fraction, 65 g, was shown by gas chromatographic analysis to consist of 0.15% dicyclopentadiene, 88.3% endo-5-(3-cyclohexen-1-yl)-2-norbornene, 6.1% exo-5-(3-cyclohexen-1-yl)-2-norbornene and two additional components present in the amount of 1.9% and 2.4% which are believed to be isomeric adducts of the formula

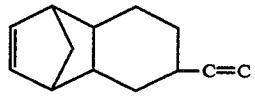

several additional components totalling about 0.4%, 0.4% tricyclopentadiene and about 0.4% unidentified components. Analysis of the fraction by nuclear magnetic resonance indicated about 87 mole percent of the endo adduct, about 9 mole percent of the exo adduct and about 5% of the isomeric adducts.

EXAMPLE 2

Preparation of Polyphenol Based on 5-(3-cyclohexen-1-yl)bicyclo[2.2.1]hept-2-ene To a reactor equipped with a stirrer, condensor and addition funnel were added 188.2 g (2.0 mole) of phenol and 1.0 g BF$_3$.Et$_2$O catalyst. The reaction mixture was heated to 70° C., and 17.4 g (0.1 mole) of 5-(3-cyclohexen-1-yl)bicyclo[2.2.1]hept-2-ene was added over a 20-minute period. The temperature was raised to 150° C. over a 1½-hour period and held for 2½ hours. Unreacted phenol was distilled. The recovered product had a melting range of 70°–80° C., a phenolic hydroxyl content of 0.495 eq/100 g and a melt viscosity of 240 cps (115° C.). The product polyphenol can be represented structurally as

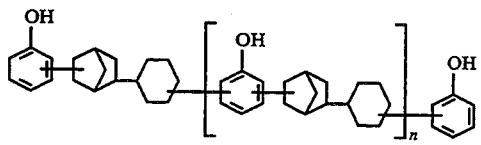

EXAMPLE 3

Preparation of Polyphenol Based on Dicyclopentadiene (Comparison)

To a reactor equipped with a stirrer, condensor and addition funnel were added 188.2 g (2.0 mole) of phenol and 1.0 g of BF$_3$.Et$_2$O catalyst. The reaction mixture was heated to 70° C. and 13.2 g (0.1 mole) of dicyclopentadiene was added over a 20-minute period and held for 2½ hours. Unreacted phenol was distilled. The recovered product had a melting range of 115°–120° C., a phenolic hydroxyl content of 0.62 eq/100 g, and a melt viscosity of 635 cps (115° C.). The product can be represented structurally as

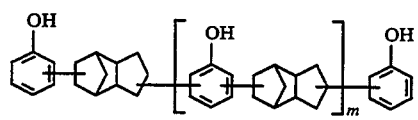

EXAMPLE 4

Preparation of Polyphenol Based on 5-(3-cyclohexen-1-yl)bicyclo[2.2.1]hept-2-ene/dicyclopentadiene To a reactor equipped with a stirrer, condensor and addition funnel were added 295.7 (3.14 mole) of phenol and 2.0 g of BF$_3$.Et$_2$O catalyst. The reaction mixture was heated to 70° C., and 13.67 g (0.07856 mole) of 5-(3-cyctohexen-1-yl)bicyclo[2.2.1]hept-2-ene and 10.29 (0.07856 mole) of dicyclopentadiene were added over a 20-minute period. The temperature was raised to 150° C. over a 1½-hour period and held for 2½ hours. Unreacted phenol was distilled. The recovered product had a melting range of 70°–78° C. The product polyphenol includes repeating structural units

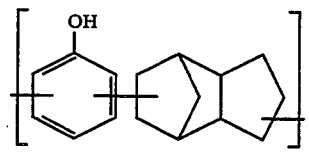

and

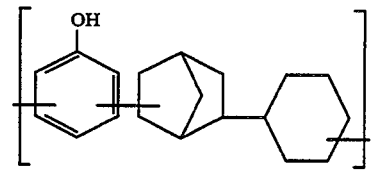

EXAMPLE 5

Preparation of Polyphenol Based on Vinylcyclohexene/Cyclopentadiene Diadduct

To a reactor equipped with a stirrer, condensor and addition funnel were added 376 g (4.0 mole) of phenol and 2.0 g of BF$_3$.Et$_2$O catalyst. The reaction mixture was heated to 70° C., and 48.g (0.2 mole) of diadduct was added over a 20-minute period. The temperature was raised to 150° C. over a 1½-hour period and held for about 2½ hours. Unreacted phenol was distilled. The recovered product had a melting range of 85°–95° C.

The product polyphenol can be represented structurally as

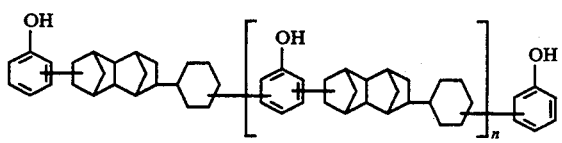

EXAMPLE 6

Preparation of Polyphenol from Mixed Dienes

To a reactor equipped with a stirrer, condensor and addition funnel were added 376 g (4.0 mole) of phenol and 2.0 g of BF$_3$.Et$_2$O catalyst. The reaction mixture was heated to 70° C., and 48 g of a diene mixture obtained from the Diels-Alder reaction of cyclopentadiene and vinylcyclohexene were added over a 20-minute period. The temperature was raised to 150° C. over a 1½-hour period and held for 2½ hours. Unreacted phenol was distilled. The recovered product had a melting range of 87°–100° C. The product polyphenol includes repeating structural units

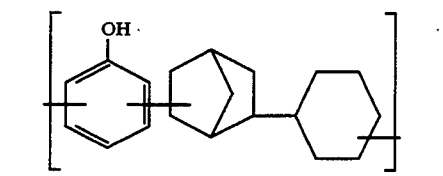

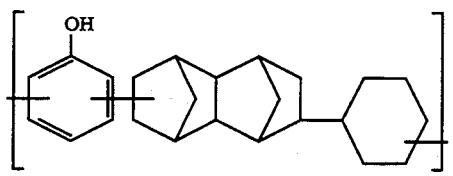

and

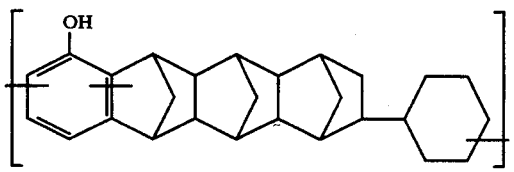

EXAMPLE 7

Cure of Epoxy Resin 27.5 g of a 67/33 (wt) blend of the diglycidyl ether of bisphenol A and tetrabromo-BPA, 4.8 g of the polyphenol prepared in Example 2 and 0.03 g 2-imidazole were melt-blended at 150° C. The mixture was then heated at 250° C. for 20 minutes. The resulting cured epoxy resin had a Tg of 91° C.

EXAMPLE 8

Cure of Epoxy Resin 27.5 g of a 67/33 (wt) blend of the diglycidyl ether of bisphenol A and tetrabromo-BPA, 4.7 g of the polyphenol prepared in Example 5 and 0.03 g 2-imidazole were melt-blended at 150° C. The mixture was then heated at 250° C. for 20 minutes. The resulting cured epoxy resin had a Tg of 91° C.

EXAMPLE 9

Cure of Epoxy Resin 2 g of the tetraglycidyl ether of the tetraphenol of ethane, 2 g of the polyphenol prepared in Example 5 and 0.03 g of 2-imidazole were melt-blended at 150° C., The mixture was then heated at 250° C. for 20 minutes. The resulting cured epoxy resin had a Tg of 185° C.

EXAMPLE 10

Cure of Epoxy Resin (Comparison)

4.08 g of a 67/33 (wt) blend of the diglycidyl ether of bisphenol A and tetrabromo-BPA, 1.61 g of the polyphenol prepared in Example 3, and 0.03 g of 2.-imidazole were melt-blended at 150° C. The mixture was then heated at 250° C. for 20 minutes, The resulting cured epoxy resin had a Tg of 118° C.

We claim:

1. A phenolic compound of the formula

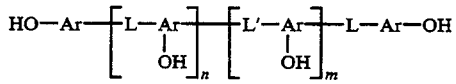

in which each Ar is a C$_{6-20}$ aromatic moiety, L is a divalent cyclohexanenorbornane moiety, L' is a divalent cycloaliphatic moiety, and each of m and n is a number within the range of 0 to 10.

2. The phenolic compound of claim 1 in which each Ar is phenyl.

3. The phenolic compound of claim 1 in which L is selected from at least one of

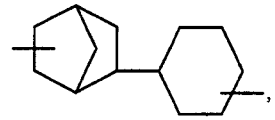

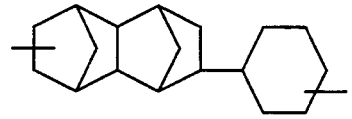

and

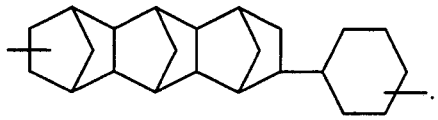

4. The phenolic compound of claim 1 in which L' is

5. The phenolic compound of claim 1 in which m is 0.
6. The phenolic compound of claim 5 in which Ar is phenyl.

7. The phenolic compound of claim 6 in which at least one L is
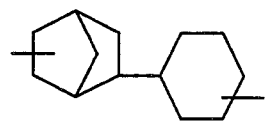
8. The phenolic compound of claim 1 in which at least one L is
and at least one L' is
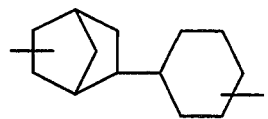
and at least one L' is
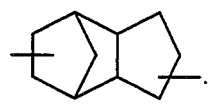
9. A composition comprising an epoxy resin and the phenolic compound of claim 1.
10. The solid product of subjecting the composition of claim 9 to a temperature of at least about 150° C. for at least about 0.25 hour.
* * * * *